Figure 1:
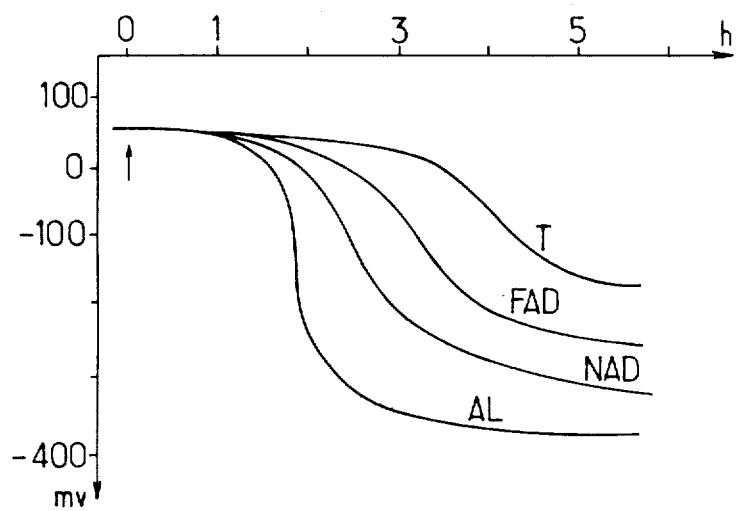

United States Patent [19]

Junter et al.

[11] 4,390,620
[45] Jun. 28, 1983

[54] METHOD AND COMPOSITION FOR THE DETECTION AND STUDY OF CELLULAR ACTIVITY OR THE LIKE AND MEANS FOR APPLYING SUCH METHOD

[75] Inventors: Guy-Alain Junter; Jean-Francois Lemeland; Eric Selegny; Jean-Claude Vingent, all of Rouen, France

[73] Assignee: Agence Nationale de Valorisation de la Recherche (ANVAR), Neuilly sur Seine, France

[21] Appl. No.: 216,911

[22] Filed: Dec. 16, 1980

Related U.S. Application Data

[63] Continuation of Ser. No. 921,706, Jul. 3, 1978, abandoned.

[30] Foreign Application Priority Data

Jul. 4, 1977 [FR] France .................. 77 20538

[51] Int. Cl.³ .................. C12Q 1/00; C12Q 1/29; C12Q 1/04; C12Q 1/06
[52] U.S. Cl. .................. 435/4; 204/1 T; 435/5; 435/7; 435/8; 435/29; 435/34; 435/39; 435/808; 435/817; 436/150; 436/904
[58] Field of Search .................. 435/4, 5, 7, 8, 29, 435/34, 35, 36, 37, 38, 39, 40, 243, 808, 817; 204/195 B, 1 E; 23/230 B; 252/408

[56] References Cited

U.S. PATENT DOCUMENTS 3,506,544 4/1970 Silverman et al. .................. 435/39 X
4,006,061 2/1977 Weeks et al. .................. 435/26

FOREIGN PATENT DOCUMENTS 1107700 3/1968 United Kingdom .

OTHER PUBLICATIONS

Albert L. Lehninger, Biochemistry, 2nd Ed. pp. 427, 450 and 477–488; 1975.

*Primary Examiner*—Robert J. Warden
*Attorney, Agent, or Firm*—Weiser, Stapler & Spivak

[57] ABSTRACT

The invention pertains to a method for the study of the behaviour or detection of cells, organites or cellular fractions, possibly present in a medium.

It comprises providing said medium with the essential nutrients to promote the activity of the said cells, organites or cellular fractions, if any, as well as with an "electron transporter" such as lipoic acid which is liable of forming a redox system and of intervening in one of the metabolic routes involved by the above said activity, particularly growth of cells.

The method of the invention then further comprises measuring and detecting a possible modification of the relative proportions of the oxidized and reduced form of the "electron transporter". The time required for such modification to possibly take place, as well as other parameters of the reaction can then be correlated to the presence in the medium concerned of a cellular activity or analogous.

97 Claims, 10 Drawing Figures

METHOD AND COMPOSITION FOR THE DETECTION AND STUDY OF CELLULAR ACTIVITY OR THE LIKE AND MEANS FOR APPLYING SUCH METHOD

This is a continuation of application Ser. No. 921,706 filed July 3, 1978 now abandoned.

The invention relates to the investigation of the possible cellular activity in a medium.

It relates more particularly to a potentiometric method for investigating cellular activity, particularly bacterial activity, in various media.

Investigation of bacterial contamination in various media such as water (river water, tap water, etc.), in biological liquids such as blood, urine, etc. or products for consumption (drinks, foods), generally brings into play methods of detection which are often difficult to apply and do not always have the desired degree of reliability.

For example, the method used at present for detecting possible contamination and determining its degree in liquids such as water or biological liquids consists of taking samples of the medium assumed contaminated, of depositing a certain amount of the samples on a solid nutrient medium and of counting the colonies after 24 or 48 hours of incubation at 37° C. It is then possible, when a contamination has been detected, for instance in biological liquids, to repeat the same experiment on nutrient media including different antibiotics in order to produce an antibiogram, whereby the one or more suitable antibiotics will then be contained in the media wherein no microbial growth is observed.

All these manipulations are complicated and the method does not provide the results sought except after time intervals which sometimes reach and even exceed 24 hours.

Such delays make it particularly difficult to carry out routine operations, for example those relating to systematically repeated survey of bacterial pollution, for example of city water or other food compositions. Other methods have thus been sought, for the detection or identification of the bacteria possibly contained in the media of the most varied types, which are at the same time simpler and more rapid, whilst preserving the desired degree of reliability.

Among these methods are comprised those which bring into play potentiometric measurements. For example, it has already been suggested to use the capacity possessed by certain bacteria, such as *Escherichia coli* and Proteus, of producing hydrogen in culture media at certain stages of their development, this hydrogen production then causing modification of the potential taken by a measuring electrode in contact with the medium relative to that of a reference electrode. In particular, it has been observed that a logarithmic relationship existed between the amount of the inoculum, on the one hand, and the time interval (latent period) necessary for the appearance of a potentiometric signal from the moment of inoculation, on the other hand.

However, the appearance of this signal is rarely distinct and therefore is a source of inaccuracies which have prevented the development of such a method. In addition, the latter is only applicable to the study of bacteria capable of producing hydrogen.

Other attempts which have hardly succeeded hitherto have borne on the potentiometric detection of oxidoreduction reactions which take place in the microorganisms and which can be influenced by the oxygen of the ambient medium.

The determination of suitable oxidoreduction potentials (or redox potentials) has however always been considered as extremely difficult, if only due to the fact that the most varied constituents which are used in the bacteria nutrient solutions (proteins, mineral salts, numerous growth factors) did not permit to accurately correlate the observed variations in potential to any specific phenomenon.

Reference is made to such a method in a document of NASA, dated February 1973 and entitled "NASA TECH BRIEF Goddard Space Flight Center" B-73-10045. This method sought to correlate the presence of bacteria in the midst of a medium kept at a temperature of about 37° C. in a closed container, to a variation in potential possibly observed between two immersed electrodes, itself connected with the consumption of the oxygen initially contained in the medium. The authors indicate however in this document that the necessary equipment for the detection of the variations in potentials in question had to be extremely sensitive, notably capable of detecting a variation of 1 mV.

It is clear that such a necessary sensitivity could prima faciae be considered as leading away from any extensive application in practice of such a method by non-specialists.

The invention is based on the discovery that certain metabolic processes can be considerably amplified by a chemical route under conditions such that these voltage variations become detectable with quite conventional equipment, thus placing at the disposal of a larger public, a method enabling investigation of the microbial behavior which can occur in the midst of a medium.

The process according to the invention of detection and investigation of the behavior of cells, organites or cellular fractions, particularly of bacteria possibly present in a medium, comprises subjecting to measuring operations said medium which has at least one exogenic compound referred to hereafter as "electron transporter" incorporated therein and which also contains, from the moment when it is desired to promote cellular activity, one or several nutrient agents selected so as to permit the development of the activity of these cells, organites or cellular fractions, if any, by one or more predetermined metabolic routes, on the one hand, and basic constituents other than these nutrient principles, but nonetheless necessary for said development, on the other hand, wherein the abovesaid electron transporter is selected from among those of the substances, notably cofactors, particularly coenzymes, which are capable both of intervening in one of the abovesaid metabolic routes and of existing in the oxidized and reduced forms of a redox system and said measuring operations aim at detecting a possible modification of the relative proportions of the oxidized and reduced forms of said electron transporter, liable of being induced at a given moment by the metabolic activity of said cells, organites or cellular fractions, if any, in the midst of said medium.

By way of example of cells, bacteria may be mentioned, but also any other form of cell, eucaryotic cells included.

The process is also applied with advantage to the investigation of any organite or cellular fraction capable of having metabolic activity, notably capable of transforming or consuming a substrate in the presence of a constituent also contained or capable of being liberated in this medium, which constituent can exist in oxidized form and in reduced form. The method according to the invention hence enables, here again, the study of such a transformation or consumption, as soon as it involves a possible variation in the relative proportions of the respectively oxidized and reduced forms of said constituent.

By way of example of organites, may be mentioned viruses, and by way of example of cellular fractions, the mitochondria.

By way of example of cells, may be mentioned bacteria, but also any other form of cells, eucaryotic cells included.

Advantageously, the method is applied in the presence of an oxidoreduction indicator, to the extent that the said electron transporter would not itself have properties enabling direct detection of the oxido-reduction phenomena which it could itself undergo.

In the case of strains which are capable of consuming oxygen, one of the essential metabolic routes employed for the development of the micro-organisms, especially when the latter are strict—or optionally aerobic germs, brings into play the oxidative decarboxylation of α-ketonic acids, for example pyruvic acid.

In accordance with a preferred embodiment of the invention, recourse is had to one at least of the electron transporters capable of intervening at this level. Among the latter, may be mentioned favine adenine dinucleotide (FAD), nicotinamide dinucleotide (NAD) and lipoic acid.

To detect and measure the possible modification of the relative proportions of the oxidized and reduced forms of the electron transporter, recourse is advantageously had to a potentiometric method bringing into play variations in the potential which are connected with the abovesaid modifications of a measuring electrode in contact with the medium under study relative to a reference electrode.

Lipoic acid of which the formula is reproduced below:

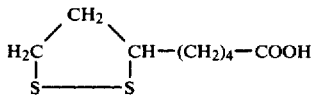

constitutes the preferred electron transporter, since it behaves both as an electron transporter and an oxydoreduction indicator.

It is observed, especially when the operation is carried out under preferred conditions which are indicated below, that the reduction of the oxidized form of the electron transporter is accompanied by a variation in the potential (potentiometric wave) which can reach 300 mV.

The two other electron transporters mentioned above give rise to the same phenomena, although in less intense and more delayed manner, at least when recourse is had to the abovesaid potentiometric method. The modifications in potential always remain still quite sufficient to be detected by means of the equipment currently used in electro-chemical laboratories, especially when the preferred experimental conditions which will be described are applied.

If necessary, the response can be amplified by associating with these other electron transporters, a certain proportion of lipoic acid by way of oxydoreduction indicator, even though it then also intervenes to a certain extent in the reduction.

Preferrably, the abovesaid electron transporters are used initially in their oxidized form, at least as regards their major portion, in particular when the medium in which germs are to be detected is oxygen.

It has in fact been observed that important variations in the potential were consecutive to the action of the cellular metabolism on the lipoic acid itself, these transformations coinciding with a substantial exhaustion of the oxygen of the medium. It has in fact been noted, especially in working with E. coli, which is an optionally aerobic organism, that a very significant potential variation takes place when the reduction of the lipoic acid by a cellular activity, bacterial in the example concerned, is not compensated by reoxidation of the transporter.

The variations in potential which are observable depend to a certain extent on the electrodes used. Generally, for the electrode which is in contact with the medium, an indicator electrode is used which is non-polarizable and inert with respect to the medium, such as notably an electrode of platinum or of gold, the latter metal being preferred by reason of the stability of the responses provided, whatever the previous mode of treatment of the electrode.

The reference electrode may be with a liquid junction, as for example a calomel electrode, (Ag-/AgCl/KCl) easily usable in the laboratory but which has a high impedance. Advantageously, in industrial applications, a metal electrode is used which is more polarizable but of less impedance formed for example of molybdenum, of tungsten or of stainless steel.

The phenomena concerned can be demonstrated in a particularly clear manner when the study is carried out in a medium such as defined above, containing by way of nutrient principle (or energy substrate) only that or those which are necessary for the development of the bacterial culture being studied according to the metabolic conditions selected and in which the abovesaid basic constituents are chosen so that they do not permit, as far as possible, other metabolic processes which could possibly interfere, even in a lesser manner, with the desired potentiometric phenomena. In particular, the use, for the constitution of the basic medium, of the mineral salts indicated in Example I below is particularly advantageous, in that they prevent to a great extent the production of hydrogen among the products of the bacterial metabolism, notably when the bacteria studied is E. coli.

In FIG. 1 are shown typical curves representing the potential drop (expressed in mV) which can be observed as a function of time (expressed in hours) in a medium saturated with oxygen at the start of the experiment, constituted from the above indicated basic constituents, seeded with an amount of E. coli germs of the order of $4.10^6$ germs, containing glucose, in the proportion of 3 mg per ml and in the presence, respectively, of lipoic acid (AL) of NAD and of FAD, in the proportion each time of 10 μg per ml for each of them. The fourth curve (T) shows the variations observable in a control to which an electron transporter has not been added at the beginning.

It is observed that the variation in potential in a control is both weaker and more delayed. In those of the samples which were supplemented with an electron transporter, a modification in the variation of potential was observed which is triggered more rapidly, whose slopes are greater, lipoic acid giving rise to the most marked phenomena.

It has been observed that, when all of the physicochemical parameters are fixed, notably the initial concentrations of oxygen of the medium, of the electron transporter and of all the other nutrient or necessary constituents for the growth of the bacteria, there exists a reciprocal relationship between the latent time (time which extends from the placing of all the abovesaid reactants together in the medium, including the germs, to the appearance of the potentiometric wave) and the importance of the starting inoculum. This relationship can be observed both in aerobiosis and in anaerobiosis. It is the existence of this relationship which is shown to be of essential importance for the numerous applications to which the invention gives rise.

Figure 2:
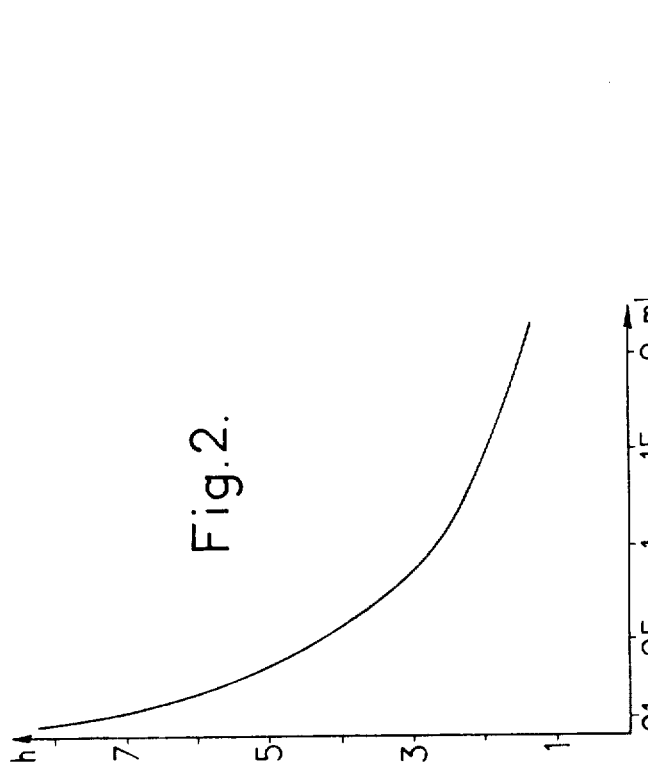

This relationship is illustrated by the curve of FIG. 2 relating to the results obtained in tests carried out under conditions similar to those which have just been described, with the exception of the variable importance of the inoculum constituted by *E. coli.* FIG. 2 shows in fact that the variation of the latent time observed (expressed in hours on the ordinate axis) as a function of the amount of inoculum (in ml of OD=0.8 on the abscissae axis of FIG. 2, it being understood that OD corresponds to the optical density of the medium measured at 546 nanometers (nm)). The abovesaid latent time relationship appears as being connected with the initial bacterial concentration, by a relationship approximately of the type $$T = \frac{a}{\sqrt{C}} + b$$

in which T is the latent time, C the initial bacterial concentration and a and b are constants.

A more accurate expression of this relationship is the following:

$$T = \frac{P}{\text{Log } 2} \cdot \text{Log } 1 + \frac{(O_2)_o}{Q_m x_o}$$

in which:
P is the time of generation, that is to say the time necessary for cellular division under predetermined conditions of the medium and of temperature;
$(O_2)_o$ is the oxygen concentration in the medium, at the moment of its inoculation with the bacterial culture;
$x_o$ is the initial concentration of germs, and
$Q_m$ a constant, representing the maximum specific speed of penetration of the oxygen, assumed identical for all bacteria appearing in the course of the culture;
(the "Log" being Naperian logarithms).

Figure 3:
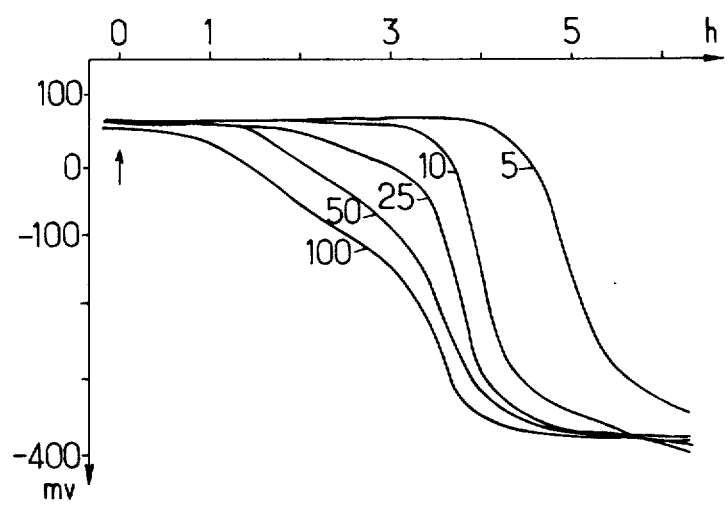

The development in the variation of potential differences observed is also a function of the concentrations of electron transporter used. This is what is established by the curves of FIG. 3 showing the variations observed when the operation is carried out in the presence respectively of 5; 10; 25; 50 and 100 μg per ml of lipoic acid, in a test carried out under aerobiotic conditions on the same medium and with an inoculum of 0.75 ml of *E. coli* of OD=0.8.

These curves show that the latent time diminishes and tends even towards 0 when the concentration of lipoic acid is very high (curve of FIG. 3 corresponding to 100 μg of lipoic acid), the slope of variation being however relatively slight. To the contrary, when the concentration of lipoic acid diminishes, the latent time becomes greater and greater, the slope of variation tending on the contrary to be steeper. Under the conditions of the experiment concerned, the steepest slopes appeared towards 25 μg of lipoic acid per ml of medium.

It rests therefore with the user to select the concentration of lipoic acid desired (it being understood that the phenomena observed appear as being of a similar nature when other electron transporters are used), in relation to the application desired, depending on whether it is desired to determine the latent time or, rather, the time necessary for a variation in the difference of potential to reach a predetermined threshold, for example −200 mV.

In practice, it appears that the concentrations of lipoic acid to be used in carrying out measurements bringing into play the above-indicated phenomena will be of the order of 10 to 100 μg per ml.

The conditions with which the medium should preferably comply to obtain the best results possible are that it has a sufficient ionic conduction to permit the electrode to record as easily as possible the variations in the potential which can be produced. The medium indicated in Example I, based principally on phosphates, is particularly favorable, in that it authorizes the variations in potential liable of being recorded to be relatively insensitive to the metabolic products released in the medium, notably when the latter is only supplemented with the energy substrates necessary for the growth of the bacteria under conditions suited to cause them to take the selected metabolic route. Another characteristic to which this medium responds is that it is buffered to a substantially neutral pH, whereby the latter remains substantially the same throughout the experiment, even when acid products of the metabolism of the bacteria are released.

In general, recourse may be had to any "base medium" (that is to say a medium which contains neither energy substrate, nor electron transporter) provided with constituents adapted to confer on this base medium, on the one hand, a sufficient ionic conduction to permit a sensitive electrode to detect variations in potential connected with oxidoreduction phenomena occuring in its midst and on the other hand, to buffer it to a pH suitable for carrying out the bacterial growth, preferably close to neutrality. Preferably, moreover, and as far as possible these constituents are selected so that the cells, organites or cellular fractions, present or introduced into this medium, are not capable of producing hydrogen among the products of their metabolism, when the one or more only energy substrates which are provided for them in this medium are those which are necessary to them to take the metabolic route which brings into action the oxidative decarboxylation of α-acetonic acids, such as pyruvic acid.

The invention relates also to the compositions themselves, which contain all the necessary ingredients, and in which may be incorporated, with a view of making the abovesaid measurements, the samples whose cellular activities are to be studied.

Such a composition is hence characterized by the association in its midst of
(a) an energy substrate selected in accordance with a growth of the micro-organisms either present or seeded into this medium, along a desired metabolic route, preferably to the exclusion of any other metabolizable substrate;

(b) mineral constituents necessary for the growth of these micro-organisms and, preferably salts contributing to ensure a high ionic conduction to this medium and acting in addition as a pH buffer, notably at neutrality;

(c) an electron transporter of the type concerned, and (d) if necessary, notably in the case where the bacterial seedings would be in reduced amount or have high demands, one or more growth factors, such as yeast extracts or other activators, for example hormonal ones.

Advantageously, the energy substrate constitutes the only source of carbon of this composition, except for the electron transporter and if necessary the oxidation-reduction indicator and the one or more growth factors.

Advantageously, a preferred medium of this type contains:

phosphates in sufficient amount to produce the above-indicated effects, glucose by way of energy substrate and/or one or several other sugars in particular of the type capable of being used in media selective with respect to certain bacteria (for example lactose for $E.coli$) and lipoic acid, preferably in its oxidized form.

Glucose is a preferred representative of the constituent sugars capable of being used by the bacterial strains, that is to say sugars that the latter can consume without previous adaptation.

Nevertheless, it is possible to replace the one or more constituent sugars by any so-called adaptive sugars, that is to say those which involve on the part of the strain under study, a prior adaptation of its metabolism, to be capable of consuming them. By way of example of such adaptive sugars, may be mentioned xylose, maltose, galactose and arabinose.

The invention relates to both media of this type, which are usable as such, upon the direct incorporation therein of the sample whose cellular activity is to be studied, and concentrated solutions of these constituents, adapted to be diluted to form the modified medium containing the adequate proportions of said constituents favorable to cellular activity.

It is of course obvious that if in numerous cases, it appears advantageous to use such compositions, in a way "ready for use", it is also possible to associate the sample whose cellular activity is to be studied in the midst of a different medium, then fed with various constituents taken separately from the above-said composition, without their order of introduction into the medium being able to be considered as having the least critical character. In particular, it is also possible to utilize liquid compositions, containing only a portion of the constituents above-mentioned, and then to introduce therein the other constituents after the incorporation into such a composition of the sample whose cellular activity is to be studied.

The sample may if necessary itself already constitute the medium containing all or part of the various constituents necessary for carrying out the measurements. This relates specifically to for example alimentary liquids, such as milk, biological media, such as blood and urine, industrial liquids where there is reason to believe that they are subject to bacterial contamination.

It will be noted in particular that if it is indispensible that the medium subjected to study should contain, from a predetermined time when it is desired to commence a measurement, both the energy substrate and the mineral constituents adapted to permit the development of the possible bacterial activity, the electron transporter may be introduced subsequently, it being understood however that it must be preferably before the moment of the possible appearance of oxidoreduction phenomena which ought to be detected. In other words, the electron transporter may be introduced into the medium before the commencement of measurements, simultaneously with the latter or subsequently to the latter. It may even be only introduced into the medium after the end of the latent time connected with the possible cellular activity in the medium, notably when the purpose of the measurements is the detection or not, after a predetermined period counting from zero time, of a cellular activity such that it is apt to produce the detectible modification, notably by potentiometry, of the proportions of the oxidized and reduced forms of the electron transporter then added to the medium.

In the foregoing, the preferred case has naturally been contemplated where the only energy substrates supplied to the medium containing the cellular activity to be studied are those necessary for the development of the cellular activity along a predetermined metabolic route. In practice, it will not always be so. This will, for example, be the case of selected media adapted for the development of the activity of certain types of bacteria to the exclusion of any other type of bacteria. The invention can nonetheless generally be applied to all media in which the oxidoreduction phenomena observable at the level of the electron transporter introduced into such media, under the action of cellular activity then present in the medium, are preponderant. If necessary, it is possible to adjust the proportions of the energy substrates of this medium, so as to increase the preponderant nature of the phenomena to be detected.

It is important, to obtain reproducible results, that the operational conditions be always the same. In particular, to the extent that variable amounts of oxygen in the medium are capable of also inducing a modification both of the latent time and of the slope of the curves which can be obtained, care should be taken to watch the stability in the various tests of the initial concentration of the dissolved oxygen in the medium.

It may be advantageous to work with a medium saturated with oxygen, each time that too high a content of this gas in the medium will not interfere with the desired development of the bacteria under study.

The potentiometric curves which can be produced vary also from one micro-organism to another. Nontheless, it will be possible for each type of micro-organism to construct graphs by fixing all the operational parameters and by studying the variation of the latent times, and even of the slopes of the potentiometric curves capable of being obtained according to the amount of the initial inoculant. These curves may be established notably under conditions which have been recalled by way of example with regard to $E.\ coli$ and with respect to FIG. 2.

It is also further possible to observe that the process according to the invention may be applied to the determination of the tolerance thresholds regarding for example bacterial contaminations of liquid media. This method consists then of checking at the end of a certain time corresponding to a threshold value, very much less than the latent time of the bacterial contaminants possibly present in the medium, either that a variation in potential is not yet recordable, or that this variation, if it has started, is not however yet manifested by a difference in potential with respect to the initial value greater than a predetermined threshold value. In the absence of such a modification, it is then possible to conclude therefrom that the medium is not contaminated, or is not contaminated beyond an acceptable threshold, whereas on the contrary the recording of such a variation at this moment or earlier enables one to conclude to the existence of a contamination exceeding the tolerable ones.

The investigational method according to the invention of the behavior of the bacteria possibly present in the midst of a medium, at least liquid in part finds various applications.

- in routine control operations, for example watching of city water or river water;
- in food industry (for example bacteriological control of milk or other food liquids, or food solids dissolved or in suspension in a liquid medium);
- in medicine, for example in research for bacterial contamination in biological liquids such as blood or urine, or also in any medium in which the activity spectrum of a given antibiotic must be evaluated;
- in routine monitoring operations of industrial liquids, such as effluents, rinsing liquids, etc., for which fear exists that they are the subject of a bacterial contamination, etc.

In practice, when city water is monitored for example, by carrying out test samplings at regular intervals and by applying to these test samples the above-described method, monitoring for a given sample and medium will be carried out for a maximum period equal to the latent time corresponding to the maximum contamination, tolerated for such water under the conditions of the study.

This detection method has great sensitivity, for example in the case of a water contaminated by colibacillus, the latent time is of the order of 12 hours, for samplings which would cause no alteration of a gelose plate after 12 hours of incubation, which corresponds to a contamination of less than 10 bacteria per ml in the sample under study.

In practice, it is possible to record the variations in potential, which permits continuous watching of the development of the bacteria and it is possible, for example by means of the illumination of a control lamp, to visualize the appearance of sufficient variation in potential. It is obviously possible to resort to any other type of warning signal (visible, sound, etc.).

It is also possible to provide for the use of a simple electronic warning system coming into operation in all cases where the latent time recorded is less than the latent time corresponding to the minimum contamination allowable by the legislation.

To carry out "semi-continuous" monitoring, it is possible to provide for carrying out detections in series corresponding to samplings effected at regular time intervals.

The method according to the invention is also applicable to an extremely important field which is that of the identification of bacteria or of the study of their behavior with regards to certain predetermined constituents introduced into the medium. These constituents, to the extent that they interfere with the bacterial metabolism, are of a nature to modify the general shape of the potentiometric curves of the micro-organisms under study whence the possibility of drawing therefrom conclusions as to their behavior.

An important application of the method according to the invention consists of the study of the behavior of cellular organisms with respect to the effect of the most varied substances, such as active principles of medicaments or other drugs, and activators or possible inhibitors or cellular metabolism, various regulators of cellular activities, for example membranal regulators, among which antibiotics.

The action of an antibiotic on bacteria, present or introduced into a medium adapted for the application of the method according to the invention, is liable of inducing a number of modifications of the curves representative of the variations of the abovesaid potential difference as a function of time. The different modifications are of a nature to provide a certain amount of information on the behaviour of such or such bacteria with respect to this or that antibiotic.

Various types of modifications have thus been demonstratable:

(1) The presence of the antibiotic is accompanied by a reduction in the amplitude of the potential drop observed, accompanied then by a rise again of the potential, manifesting notably a secondary reoxidation of lipoic acid. This case is encountered for those antibiotics which block on a short term the microbial activity and which are of lethal effect with respect to the bacteria. This is in particular the case of bactericidal antibiotics.

(2) There is observed in the presence of the antibiotic, either a reduction in the slope of the potential variation, connected with the oxidoreduction reaction applied by the method according to the invention, or an increase in latent time: these modifications are observed for those antibiotics which, at the doses studied, reduce the growth rate or only inhibit partially the bacterial metabolism. This is notably the case of bacteriostatic antibiotics.

For example, the following modifications are observed with respect to the regulators of cellular activities indicated below:

a reduction of amplitude with secondary reoxidation for:
the $\beta$-lactamines: inhibition of synthesis of the cell wall,
the aminosides: disturbance of the protein synthesis at the level of the 30 S ribosome,
nalidixic acid: inhibition of the synthesis of desoxyribonucleic acid;
a reduction in the slope for:
chloramphenicol: inhibition of protein syntheses at the level of 50 S ribosome,
polymyxin: alteration of the membrane;
an increase in the latent time for:
rifamycine: inhibition of the synthesis of RNA,
the macrolides and related substances: disturbance of the protein syntheses at the level of ribosome 50 S.

(The nature of the actions of these various regulators has also being indicated).

The method according to the invention enables comparative studies of the effect of various regulators with respect to various organisms or cellular fractions, for example comparisons of the effects of various antibiotics with respect to a particular bacterial species, or to the contrary, of the same antibiotic with respect to various bacterial species.

Numerous possibilities of the present invention in this field will also be indicated in the way of examples of which the purpose is to illustrate further the invention, of course in non-limiting manner.

EXAMPLE I

Use of a "Minimum" Base Medium

In all the tests which follow, the culture was carried out in a flask of about 60 ml capacity, with two tubes which can be closed in fluid-tight manner with respect to the ambient air in the course of the microbial growth, so that the amount of oxygen available to the bacteria after seeding is constant. One of the tubes serves for the introduction of various constituent elements of the medium and the other tube serves for the introduction of a combined or/calomel electrode which is directly connected to a potentiometric recorder.

The volume of the culture medium utilized in the course of a test is constant and equal to 35 ml.

The minimum "base medium" has the following composition (proportions related to 1 liter of distilled water):

| | | | |
|---|---|---|---|
| $K_2H\ PO_4$ | 10.5 g | $FeSO_4, 7H_2O$ | 5 mg |
| $H_2K\ PO_4$ | 3.5 g | $CaCl_2, 2H_2O$ | 50 mg |
| $NH_4\ Cl$ | 0.5 g | $MnCl_2, 4H_2O$ | 5 mg |
| $MgSO_4, 7\ H_2O$ | 0.050 g | | |

For each test, 35 ml of this base medium were used to which were added, before inoculation, an energy substrate and an electron transporter.

In the tests 1, 2 and 3 which follow the energy substrate is constituted by 0.2 ml of a solution with 30% by weight of glucose and the electron transporter is constituted by 0.2 ml of 1 mg/ml of lipoic acid solution.

The flask is closed in fluid-tight manner before starting the measurements.

Test 1:

35 ml of base medium, supplemented with glucose and lipoic acid in the proportions indicated above, are placed in a flask and shaken vigorously until the equilibrum ($O_2$) air$\rightleftharpoons$($O_2$) dissolved is reached. The medium is seeded by 1 ml of an *Escherichia coli* culture of optical density 0.8 for a reading effected at 546 nm, which corresponds to about $176.10^6$ germs. The flask is closed and the variations in potential as a function of time are recorded.

It is observed that the potential decreases suddenly after 2 h 20 min. of culture, which corresponds to a deoxygenation-reduction potentiometric "wave".

Test 2:

The culture medium used is the same as that of Test 1 (base medium+glucose+lipoic acid) but there is added to it 0.4 ml of 20% yeast water to favor the growth of the bacteria. This medium is deoxygenated by bubbling therethrough for 15 minutes a current of nitrogen (medical nitrogen supplied by the Company L'AIR LIQUIDE the partial pressure of dissolved oxygen is then less than 10 mm Hg.

0.01 ml of the culture of colibacillis used in Example I, namely $175.10^4$ germs, is inoculated and the cultivation is carried out under a current of nitrogen. The potentiometric "wave" appears at the end of 3 h 20 min. after seeding.

Test 3:

The composition of the culture medium is the same as in the preceding case but there is added to it an additional growth factor namely thiamine pyrophosphate (TPP) in the proportion of 0.4 ml of an 0.1 mg/ml solution.

The medium is shaken with free air as in Test 1, and then seeded by a very dilute culture of *Escherichia coli* (conventional numbering of a gelose plate indicates that the germ concentration immediately after inoculation is 100 bacteria per ml). The flask is closed and the potentiometric recording is carried out. A latent time of 7 hours 10 minutes was then recorded.

Test 4:

The same experimental conditions as in Test 1 were utilized upon replacing the glucose by another energy substrate, namely:

either 0.5 ml of a solution of 50 mg sodium pyruvate/ml, or 0.4 ml of a solution of 50 mg levulose/ml, or 0.4 ml of a solution of 50 mg galactose/ml, or 0.4 ml of a solution of 50 mg lactose/ml The resulting signals are comparable with those obtained with glucose but the latent time and the slope of the potential wave depends on the substrate employed; with pyruvate, the signal is delayed with respect to those which are observed with various sugars. Hence the bacterial growth is slow in the presence of the first mentioned substrate.

In the following table, are collected the results obtained by using the conditions of Test 1 (glucose substrate) or again under the conditions of Example 4 (levulose, galactose, pyruvate or lactose substrate).

In this table are shown, on the one hand, the time intervals required for the appearance of the signal and, on the other hand, the time intervals required by the potential difference to vary by an amount of 200 mV in the presence of various substrates.

| | glucose | levulose | galactose | pyruvate | lactose |
|---|---|---|---|---|---|
| Start signal | 3h 15 | 2h 20 | 2h 30 | 7h 35 | 3h 20 |
| 200mV | 4h 30 | 4h 30 | 8h 20 | 12h | 5h 20 |

The very favorable results which are observed show the extent at which it is possible to select the most suitable parameters according to the nature of any application.

EXAMPLE II

Application to the Determination of Contamination in Various Media

Preparation of the Base Medium

A solution seven times more concentrated in its various constituents than the base medium used in Tests 1 to 4 was made up, so that the mixing of 5 ml of this concentrated solution with 30 ml of liquid called below "support", whose bacterial contamination had to be studied, led to a modified support containing proportions of mineral salts identical to those of the base medium of the preceding example.

In all cases the modified support which is thus obtained is supplemented, before starting the measurements, with glucose and lipoic acid, in concentrations indicated in Example I, and growth activators such as yeast water or thyamine pyrophosphate (TPP), at the concentrations indicated in Test 3 of the preceding example.

In this example two supports were used, namely:
milk containing initially 100 grams per milliliter, tap water containing 30 germs per milliliter (the germs contained in these two supports were initially numbered on a gelose plate).

By operating under the above-indicated conditions, it was observed, in the case of milk, that there was a variation of 200 mV, in the potential difference measured at the end of 10 hours. The same variation was observed in the tests carried out on water at the end of 13 hours.

Taking these results into account, it is observed that the operational conditions which have been described (or any other similar operational conditions) could be applied in a system which would be utilized for carrying out systematic, possibly automatic and/or semi-continuous checking of the bacteriological quality of water or of milk. By strictly applying the above indicated operational conditions, it can reasonably be estimated that, according to French official standards, town water would not be biologically polluted if it does not give rise, under the same experimental conditions, to the appearance of a modification in the potential difference initially measured at the end of 13 hours.

According to these standards the level of bacteria in potable water must not exceed 30 to 50 bacteria per ml.

The invention lends itself naturally to automatization or semi-automatization permitting repetitive monitoring.

Figure 4:
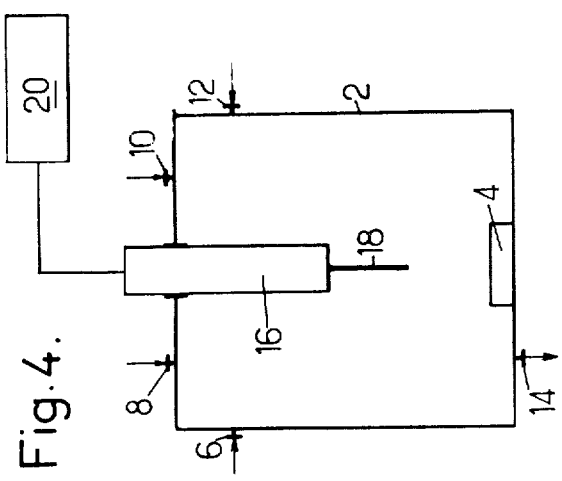

In FIG. 4 is shown a diagram of an installation permitting repetitive monitoring with cyclic checking of the bacterial contamination. The installation includes an enclosure or tank 2 (having for example a volume of 100 ml) provided with means (not shown) enabling it to be thermostated at 37° C., stirrers (such as a magnetic stirrer 4), inlet valves 6,8, 10 and 12 and draining valve 14. A potentiometric recorder, shown diagrammatically at 16, including as known in itself, a measuring electrode 18 designed to dip into the medium under study and a reference electrode (not shown) associated therewith. The data supplied by this potentiometric recorder can be directed to a central memory 20 or the like, capable of utilizing the results obtained.

The repetitive monitoring then includes the measuring cycles comprising respectively:
  introducing a standardized test sample into the tank, through valve 6,
  introducing air through valve 10 and the reactants (mineral salts, growth factors, glucose or energy substrates, one or several electron transporters) through valve 12,
  stirring in the presence of air to saturate the medium with oxygen,
  closing all the valves,
  monitoring the potential in the medium during a predetermined time interval, such as that imposed by particular monitoring standards, by means of a potentiometric device advantageously provided with a warning equipment capable of producing a signal in case of bacterial contamination
  draining the tank through the valve 14 (the valve 10 open),
  rinsing the tank (rinsing water introduced through the valve 6 and detergent if necessary introduced through the valve 8), and
  and sterilizing the tank, the latter then being ready for a new measuring cycle.

Of course, these operations, notably the opening and closing of the valves, are actuated automatically according to the functions which must be carried out by the whole of the system.

EXAMPLE III

Test 1:

The same base medium was still used and the same conditions of oxygenation as in the preceding examples were used. The base medium was however supplemented to contain the following constituents:
  glucose: 0.2 ml of a 30% solution
  TPP: 0.1 ml at 0.1 mg/ml
  20% yeast water: 0.4 ml
  coenzyme A: 0.1 to 1 mg/ml
  NAD: 0.1 to 1 µg/ml
  DAD: 0.1 to 1 µg/ml
  lipoic acid: 0.2 ml of a 1 mg/ml solution The medium is, before the measurements, seeded by 2 ml of a culture of *Staphylococcus epidermidis* of optical density 0.8, which corresponds to about 350 million germs. A sudden potential variation appears 1 hour and 30 minutes after the inoculation.

The tests which follow are carried out in conventional selection media (instead of the base medium of the preceding example).

Test 2: Chapman medium (used to isolate the pathogenic staphylococci).

It contains (proportions related to 1 liter of distilled water):
  beef extract: 1 g
  polypeptone: 10 g
  sodium chloride: 75 g
  d. mannitol: 10 g
  phenol red: 0.025 g.

To 35 ml of this medium are added 0.2 ml of 30% glucose solution and 0.2 ml of 1 mg/ml lipoic acid solution. The medium was saturated with oxygen and inoculated with an inoculum of colibacilli comprising approximately $5.10^6$ germs before closing the flask and starting the measurements. A potential variation of 200 mV was observed at the end of 9 h 25 minutes.

Test 3:

By operating under the same conditions as in Test 2, but with an inoculum of staphylococci, a signal corresponding to a variation in potential of 200 mV was observed at the end of 4 h 15 minutes.

Test 4:

Use of a culture medium based on "brilliant green".

This medium is known to serve for the isolation of Salmonellae.

The composition of this medium is as follows (related to 1 liter of distilled water):
  yeast extract: 3 g
  polypeptone: 10 g
  sodium chloride: 5 g
  lactose: 10 g
  saccharose: 10 g
  phenol red: 0.08 g
  brillant green: 0.0125 g To 35 ml of this medium is added glucose and lipoic acid. The mixture is saturated with oxygen under the same conditions as in Example I.

The development of the potentials of two cultures initiated differently but with the same overall amount of germs, was followed in parallel.

First Flask:

The mixture comprised equivalent proportions of three strains, namely *E. coli*, *Salmonella typhimurium* and *Staphylococcus epidermidis;* the difference in potential starts to vary at the end of 10 hours after the seeding and reaches 200 mV after 13 h 30 of cultivation.

Second Flask:

A mixture of two strains in equivalent proportions was used, namely *E. coli* and *Staphylococcus epidermidis* the variation in potential starts to vary at the end of 10 hours and reaches 200 mV after 20 hours of cultivation.

EXAMPLE IV

This example is aimed at showing the behavior of blood and urine samples in potentiometry, when contaminated with a particular amount of germs.

(1) Tests on Blood:

35 ml of blood suspended in the conventional medium for blood culture supplied by the PASTEUR INSTITUTE, were contaminated at time zero (according to the scale of the abscissae of FIG. 5) by about $10^4$ germs of *E. coli*. 0.2 ml of 1 mg/ml lipoic acid solutions is added at the beginning of the measurement. The curve I is representative of the variation in the potential difference measured in the cell under the same conditions as in Example I, as a function of time. It is observed that the variation in potential which is recorded as a result of the oxidoreduction reaction of the lipoic acid, is higher than 300 mV.

It has not been necessary, in this case, to add a substrate (glucose) to the medium which was sufficiently rich in nutrient substances and in mineral salts to permit the desired oxidoreduction reaction.

Figure 5:
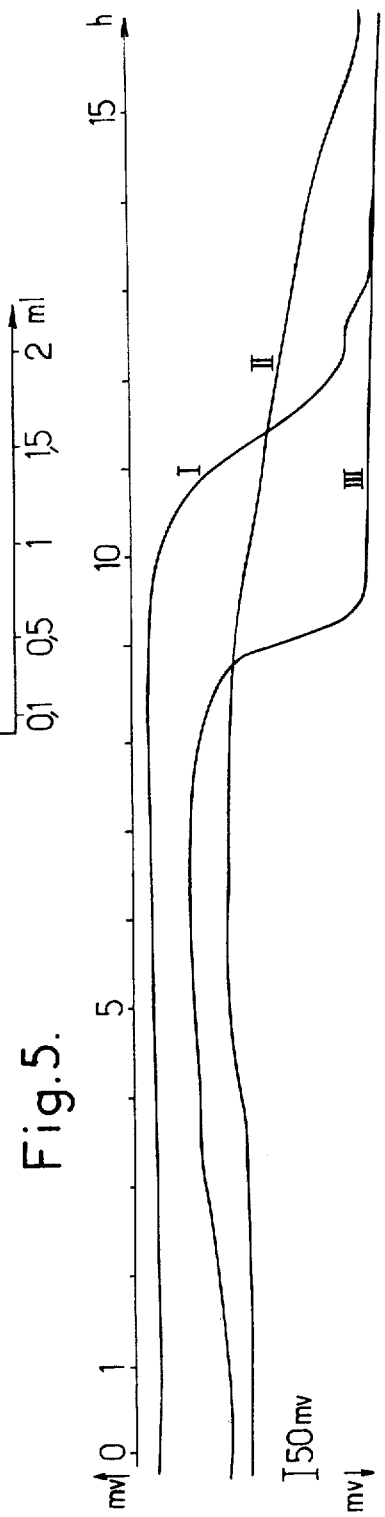

(2) Tests on Urine:

The two media studied below were both contaminated at time zero by $10^4$ germs of *E. coli*.

a. Tests on urine directly:

Under similar conditions, a study was carried out of the variation in differences of potential which were observed in 35 ml of human urine upon addition of 0.2 ml of lipoic acid in the proportion of 1 mg/ml and 0.2 ml of a 30% glucose solution. The curve II of FIG. 5 is representative of the phenomena observed. The absence of a distinct "potentiometric wave" is noted.

b. Tests on the same urine enriched with mineral salts:

To the contrary, a very distinct "potentiometric wave" is obtained (curve III, FIG. 5) when the potentiometric measurements are carried out in the medium formed by 30 ml of the same urine to which 5 ml of the concentrated solution has been added, seen in Example II, and of the same amounts of glucose and lipoic acid as in the preceding test.

EXAMPLE V

This example seeks to illustrate the various types of modifications which can be induced by antibiotics on the cellular development of various bacterial species.

The cultures were carried out at 37° C., under aerobiosis, with stirring (60 rpm) in double necked 50 ml ERLEN MEYER flasks, one neck being occupied by the combined electrode (non-polarizable gold measuring electrode/calomel electrode), the other neck serving for the introduction of the products.

The tests were carried out in the minimum base medium (described in Example I) containing 3 g of glucose/1000 forming a final volume (culture medium plus inoculum) of 40 ml and containing 24 $\mu$g/ml of lipoic acid. The seedings were carried out with inoculi of 2 ml of a culture on the same minimum medium in the exponential growth phase, adjusted to an OD of 0.5 at 546 nm, at a final concentration of about $5.10^8$ bacteria/ml.

The antibiotics tested were utilized at doses which will be indicated below with respect to the description of each of the tests.

Test 1:

The antibiotic used is penicillin and the microorganism studied is *Staphylococcus aureus*.

The antibiotic doses utilized are respectively 0.1, 0.05 and 0.02 units/ml.

Figure 6:
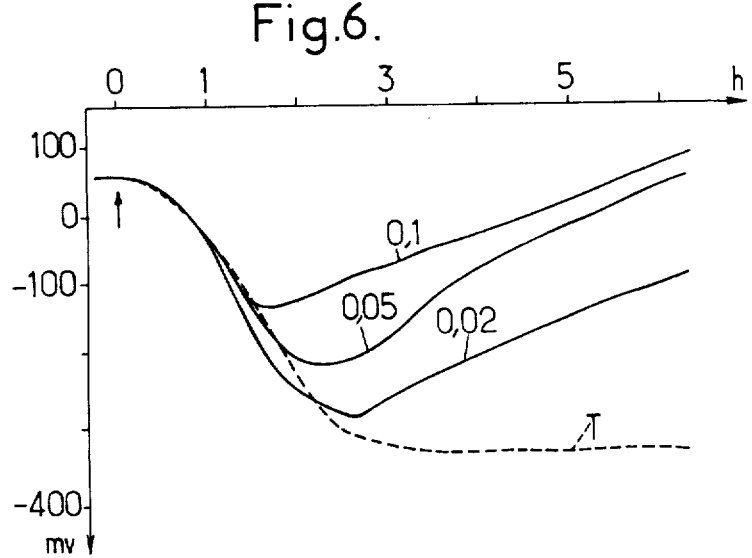
Figure 7:
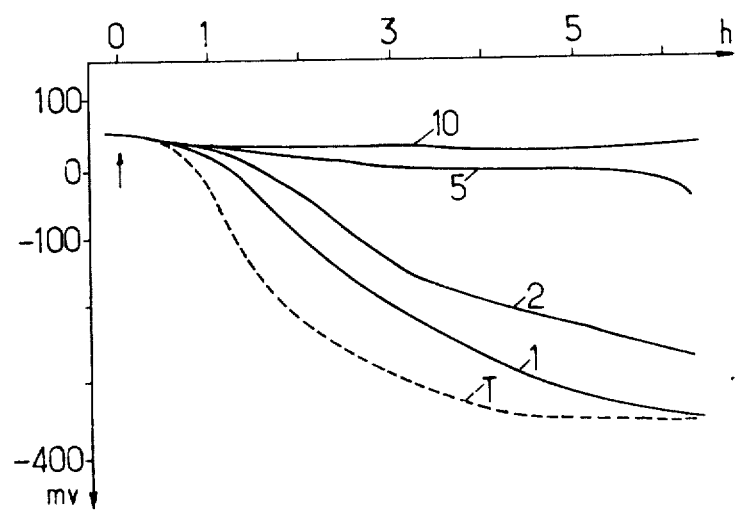

The curves of FIG. 6 are representative of the variations in potential difference, as a function of time, which are observed in the presence of these various doses. The curve T corresponds to the variation of this potential difference in a control.

As can be observed, the modification bears essentially on the amplitude of the signal: at a given moment, dependant on the concentration of antibiotic in the medium, the variation in potential which is observed comes to a stop which is then followed by a rapid increase of the potential corresponding to the reoxidation of the medium consequent upon metabolic blocking. Penicillin behaves in this test like a bactericid.

Test 2:

In this test, the antibiotic tested was chloramphenicol (in the amount of 1, 2, 5 and 10 $\mu$g/ml) and the microorganism studied was *Staphylococcus aureus*.

The curves of FIG. 6 are representative of the phenomena observed. There is observed essentially a modification of the slope of the curves without secondary oxidation and without modification of the final potential, except for high doses, which are rapidly lethal. When a dose of 10 $\mu$g/ml of chloramphenicol is present, no variation in potential is even observed after inoculation of the bacteria. At low doses, it behaves, in the test concerned, as a bacteriostatic agent.

Test 3:

The antibiotic used was rifamycine in the proportion of 1,2 and 5 $\mu$g per ml in the various tests, and the micro-organism used was *E. coli*.

Figure 8:
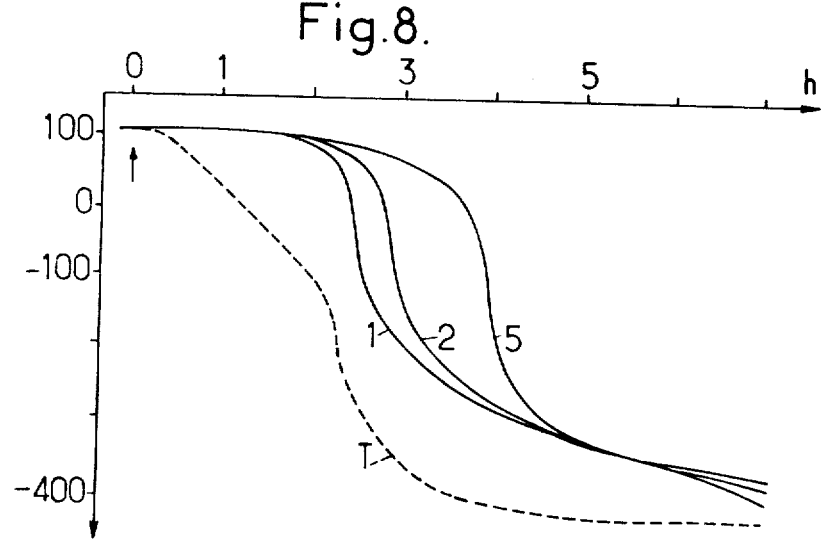

The curves of FIG. 8 were representative of the phenomena observed in each of these cases as well as in a control (curve T). The modifications observed for this antibiotic are very characteristic. There is an increase in the latent time, and especially an increase in the slope of the curve. This antibiotic behaves rather as a bacteriostatic agent.

Figure 9:
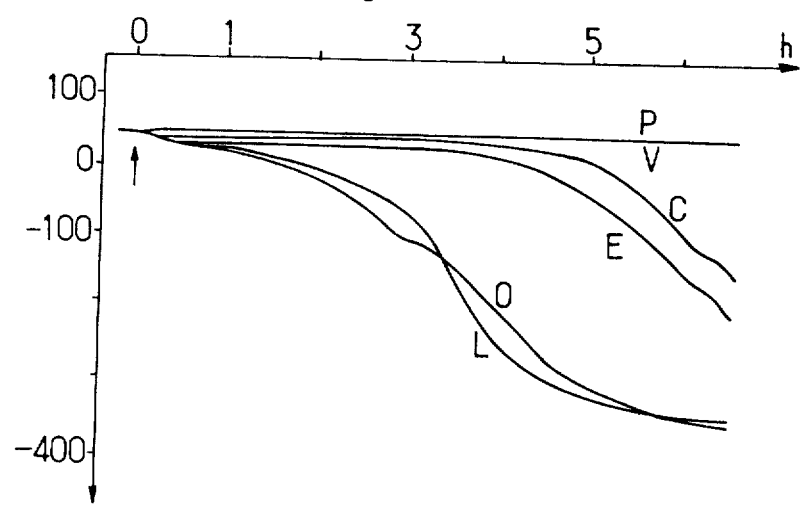

Test 4:

Six antibiotics were tested on *Staphylococcus aureus* at the concentration of 0.5 $\mu$g per ml. The curves of FIG. 9 are representative of the phenomena observed for each of them: erythromycine (E), oleandomycine (O), lincomycine (L), clindamycine (C), virginiamycine (V), and pristinamycine (P).

The modifications bear on the latent time and the variations in potential. The corresponding curves show that lincomycine and oleandomycine are less active: then come erythromycin and clindamycin. Virginiamycin and pristinamycin are the most effective.

This example demonstrates the extent at which enables an easy distinction to be made between the activities of various types of antibiotics with respect to a particular bacteria.

Test 5:

This study was carried out on *E. coli* K12. It is designed to show the application of the method according to the invention to the study of the effect of antibiotic associations, compared with the effects of the corresponding antibiotics taken separately.

The antibiotics used in the test concerned were gentamycin (G), in the proportion of 0.5 $\mu$g per ml, and rifamycin (R), in the proportion of 1 $\mu$g per ml.

Figure 10:
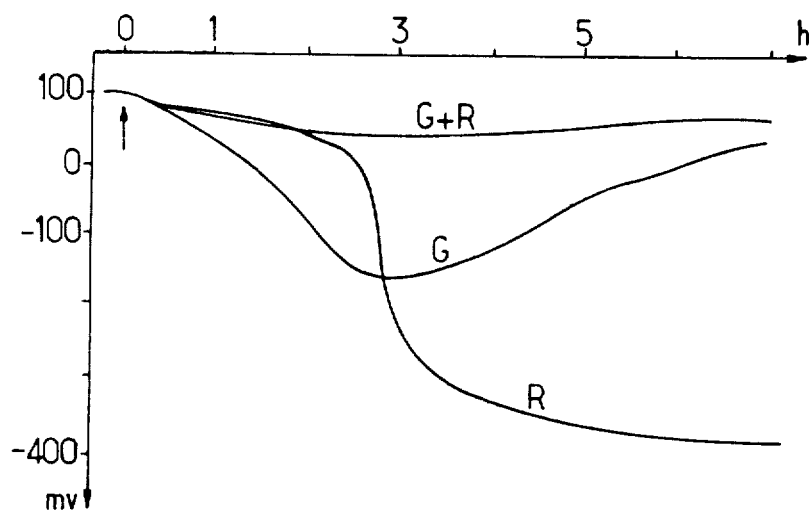

The curves FIG. 10 are representative of the effects observed with respect to each of the antibiotics taken separately and with the association G+R.

The examination of the curves shows a synergistic effect. Whereas with each of the antibiotics taken separately, it is observed that the bacterial culture could give rise to cellular development, even if it was limited, the association of the two antibiotics completely blocked its development.

In the two preceding examples, the electrodes were constituted:

as regards the measuring electrode, by gold, and
as regards the reference electrode, by a calomel electrode (such as marketed by the company named TACUSEL, type C8).

It will be noted that—except in the case of strict anaerobic bacteria—the studies can be made either in the open air, or in a controlled atmosphere, or in a closed container.

As is self-evident and as emerges already from the foregoing, the invention is in no way limited to those of its embodiments and types of application which have been more especially envisaged; it emcompasses on the contrary all modifications. Among these modifications, may be mentioned, with regard to the method of detection of the oxidoreduction phenomena sought, techniques other than potentiometry, for example that bringing into play colored indicators. By way of indication, it is mentioned that colored indicators capable of visualizing oxidoreduction phenomena such as has been described in the foregoing, are identified notably in the book of CHARLOT entitled "The Methods of Analytical Chemistry", Masson, pages 316-322, Edition of 1966; it is also possible to detect the relative variations in concentrations of the reduced form and oxidized form respectively of the electron transporter by other non-electrochemical methods for example by spectrophotometry in the case of transparent media.

We claim:

1. A method for determining the presence or absence of cells, cellular fractions or organites in a liquid medium, said method comprising:
   (1) mixing
      (A) a liquid medium having sufficient ionic conductivity to permit potentiometric measurements, a pH buffered about 7.0, and containing an energy substrate selected from those which cells, cellular fractions or organites are known to metabolize by at least one metabolic route with
      (B) an electron transporter having an initial ratio of oxidized to reduced forms selected from those electron transporters which are a known part of at least one of said metabolic routes, whereby the metabolic activity of the cells, cellular fractions or organites induces a change in the initial ratio of oxidized to reduced form of said electron transporter causing a change in potential of said liquid medium, and
   (2) measuring the potential of the medium as a function of time to determine the change in potential which resulted from said change in the ratio of oxidized to reduced form of the electron transporter, said change in ratio having resulted from the metabolic activity of cells, cellular fractions or organites during the time period over which measurements were made, and
   (3) relating the change in potential to the presence or absence of cells, cellular fractions or organites in the liquid medium at the time when the measurements were commenced.

2. The method of claim 1 wherein a change in potential is observed, thereby indicating a presence, rather than absence of cells, cellular fractions or organites.

3. The method of claim 1 wherein no change in potential is observed, thereby indicating an absence rather than a presence of cells, cellular fractions or organites.

4. The method of claim 1 wherein the measurements of potential are continuous.

5. The method of claim 1 wherein the measurements are intermittent.

6. The method of claim 1 wherein a minimum of two measurements of the potential are made.

7. The method of claim 1 wherein the electron transporter is mixed with the liquid medium at a time no later than the time at which a change in potential would occur if the electron transporter had been mixed at the commencement of measurements.

8. The method of claim 1 wherein the cells are bacteria.

9. The method of claim 8 wherein the bacteria are aerobic.

10. The method of claim 8 wherein the bacteria are optionally aerobic.

11. The method of claim 8 wherein the bacteria are selected from the group consisting of *E. Coli, Staphylococcus aureus, Staphylococcus epidermidis,* and *Salmonella typhimurium.*

12. The method of claim 1 wherein the cells are eukaryotic.

13. The method of claim 1 wherein the cellular fractions are mitochondrial fractions.

14. The method of claim 1 wherein the organites are viruses.

15. The method of claim 1 wherein the metabolic route is the route by which alpha-ketonic acids are decarboxylated.

16. The method of claim 15 wherein the alpha-ketonic acid is pyruvic acid.

17. The method of claim 1 wherein the electron transporter is a coenzyme.

18. The method of claim 17 wherein the coenzyme is selected from those coenzymes which are a known part of the metabolic route by which alpha-ketonic acids are decarboxylated.

19. The method of claim 18 wherein the alpha-ketonic acid is pyruvic acid.

20. The method of claim 19 wherein the coenzyme is selected from the group consisting of lipoic acid, NAD and FAD.

21. The method of claim 17 wherein the electron transporter is in the oxidized form.

22. The method of claim 1 wherein the electron transporter is a cofactor.

23. The method of claim 1 wherein the energy substrate is a constituent sugar.

24. The method of claim 23 wherein the sugar is glucose.

25. The method of claim 23 wherein the sugar is lactose.

26. The method of claim 1 wherein the energy substrate is an adaptive sugar.

27. The method of claim 26 wherein the adaptive sugar is selected from the group consisting of xylose, maltose, galactose, and arabinose.

28. A method for determining the initial concentration of cells which are capable of cellular division in a sample containing an unknown concentration of a known type of said cell, said method comprising:

(1) preparing several aliquots of a liquid medium having a pH buffered about 7.0, a sufficiently high ionic conductivity to permit potentiometric measurements, and comprising an energy substrate selected for its ability to promote metabolic activity of said cells by at least one metabolic route, and an electron transporter selected from those electron transporters which are a known part of said metabolic route;

(2) preparing several inocula comprising the known type of cell, each of the several inocula containing a different but known concentration of said cells;

(3) inoculating the several aliquots of liquid medium with one of the inocula containing a known concentration of said cells;

(4) inoculating at least one aliquot with the sample whose concentration is unknown;

(5) measuring the potential of each aliquot as a function of time;

(6) determining the time at which a potentiometric wave occurs in each aliquot, thereby determining the latent time of each aliquot;

(7) constructing a standard curve showing concentration of cells in the inocula containing known cell concentrations as a function of the latent time of the liquid medium into which these inocula were inoculated;

(8) determining from the standard curve the concentration of cells in the sample whose concentration of cells was unknown using the latent time of the aliquot into which this sample was introduced, thereby determining the concentration of cells which are capable of cellular division in the sample containing an unknown concentration of a known type of cell.

29. The method of claim 28 wherein the cells are bacteria.

30. The method of claim 29 wherein the bacteria are *E. Coli*.

31. The method of claim 28 wherein the measurements of potential are continuous.

32. The method of claim 28 wherein the measurements are intermittent.

33. The method of claim 28 wherein the metabolic route is the route by which alpha-ketonic acids are decarboxylated.

34. The method of claim 33 wherein the alpha-ketonic acid is pyruvic acid.

35. The method of claim 28 wherein the electron transporter is a coenzyme.

36. The method of claim 35 wherein the coenzyme is selected from those coenzymes which are a known part of the metabolic route by which alpha-ketonic acids are decarboxylated.

37. The method of claim 36 wherein the alpha-ketonic acid is pyruvic acid.

38. The method of claim 37 wherein the coenzyme is selected from the group consisting of lipoic acid, NAD and FAD.

39. The method of claim 35 wherein the electron transporter is in the oxidized form.

40. The method of claim 28 wherein the electron transporter is a cofactor.

41. The method of claim 28 wherein the energy substrate is a constituent sugar.

42. The method of claim 41 wherein the sugar is glucose.

43. The method of claim 41 wherein the sugar is lactose.

44. The method of claim 28 wherein the energy substrate is an adaptive sugar.

45. The method of claim 44 wherein the adaptive sugar is selected from the group consisting of xylose, maltose, galactose, and arabinose.

46. A method for determining the behavior of cells or cellular fractions in a liquid medium in response to a selected constituent introduced into the medium, said method comprising:

(1) preparing at least two aliquots of a liquid medium containing said cells and having a pH buffered about 7.0, a sufficiently high ionic conductivity to permit potentiometric measurements, and comprising an energy substrate selected for its ability to promote metabolic activity of said cells or cellular fractions by at least one metabolic route, and an electron transporter selected from those electron transporters which are a known part of said metabolic route;

(2) introducing a selected constituent into at least one of said aliquots, keeping at least one aliquot devoid of the selected constituent;

(3) measuring the potential of each aliquot as a function of time;

(4) determining the time at which a potentiometric wave occurs in each aliquot, thereby determining the latent time;

(5) determining the slope of the variation of potential of each aliquot;

(6) comparing the amplitude of potential, latent time and slope of the aliquots containing the selected constituent with the amplitude of potential, latent time and slope of the aliquots devoid of said constituent, thereby determining the behaviour of the cells in the liquid medium in response to the selected constituent.

47. The method of claim 46 wherein the cells are bacteria.

48. The method of claim 46 wherein the selected constituent is a drug.

49. The method of claim 46 wherein the selected constituent is a cellular regulator.

50. The method of claim 49 wherein the cellular regulator is a metabolic activator or metabolic inhibitor.

51. The method of claim 46 wherein the selected constituent is at least one antibiotic.

52. The method of claim 46, 47 or 51 wherein the comparison of amplitudes of potential reveals a lower amplitude of potential drop, followed by a rise in potential in the aliquot containing the antibiotic, thereby indicating that the antibiotic blocks for a short term the microbial activity of the bacteria.

53. The method of claims 46, 47 or 51 wherein the comparison of latent times and slopes reveals either a reduced slope or increased latent time in the aliquot containing the antibiotic, thereby indicating that the antibiotic partially inhibits metabolism of the bacteria or reduces the growth rate.

54. The method of claims 46 or 49 wherein the response of said cells to more than one regulator is determined, thereby allowing for a study of the combined effects of the regulators.

55. The method of claims 46, 47 or 51 wherein the response of more than one type of cell to a single antibiotic is determined.

56. The method of claim 46 wherein the measurements of potential are continuous.

57. The method of claim 46 wherein the measurements are intermittent.

58. The method of claim 46 wherein the metabolic route is the route by which alpha-ketonic acids are decarboxylated.

59. The method of claim 58 wherein the alpha-ketonic acid is pyruvic acid.

60. The method of claim 46 wherein the electron transporter is a coenzyme.

61. The method of claim 60 wherein the coenzyme is selected from those coenzymes which are a known part of the metabolic route by which alpha-ketonic acids are decarboxylated.

62. The method of claim 61 wherein the alpha-ketonic acid is pyruvic acid.

63. The method of claim 62 wherein the coenzyme is selected from the group consisting of lipoic acid, NAD and FAD.

64. The method of claim 60 wherein the electron transporter is in the oxidized form.

65. The method of claim 46 wherein the electron transporter is a cofactor.

66. The method of claim 46 wherein the energy substrate is a constituent sugar.

67. The method of claim 66 wherein the sugar is glucose.

68. The method of claim 66 wherein the sugar is lactose.

69. The method of claim 46 wherein the energy substrate is an adaptive sugar.

70. The method of claim 69 wherein the adaptive sugar is selected from the group consisting of xylose, maltose, galactose, and arabinose.

71. A method for determining whether a predetermined acceptable level of bacterial contamination in a liquid sample has been exceeded, said method comprising:
(1) mixing
  (A) a liquid medium having sufficient ionic conductivity to permit potentiometric measurements, a pH buffered about 7.0, and containing an energy substrate selected from those which bacteria are known to metabolize by at least one metabolic route, and containing the contents of a liquid sample, itself containing a predetermined acceptable level of bacterial contaminants with
  (B) an electron transporter having an initial ratio of oxidized to reduced forms selected from those electron transporters which are a known part of at least one of said metabolic routes, whereby the metabolic activity of the bacterial contaminants induces a charge in the initial ratio of oxidized to reduced form of said electron transporter causing a change in potential of said medium, and
(2) measuring the potential of the medium as a function of time to determine the change in potential which resulted from said change in the ratio of oxidized to reduced form of the electron transporter, said change in ratio having resulted from the metabolic activity of said bacterial contaminants during the time period over which measurements were made, and
(3) selecting a time between the time at which a change in potential first occurs and the time at which the potential reaches a minimum value, and
(4) calculating the difference between the potential of the medium at this preselected time and the potential at the commencement of measurements, thereby determining a threshold potential difference corresponding to a predetermined acceptable level of bacterial contamination, and
(5) repeating step (1) under identical physico-chemical conditions with the exception that the medium comprises the contents of a liquid sample whose level of bacterial contamination is unknown, and
(6) measuring the potential of the medium of step (5) at least twice, as soon as mixing is complete, and, again, at the time selected in step (3), and
(7) calculating the difference between the two potentials measured in step (6), and
(8) comparing the difference in potential calculated in step (7) with the threshold potential difference calculated in step (4),
whereby a difference in potential as measured in step (7) greater than the threshold potential difference is indicative of a level of bacterial contamination in the liquid sample of step (5) greater than the predetermined acceptable level and a difference in potential as measured in step (7) less than the threshold potential difference is indicative of a level of bacterial contamination in the liquid sample of step (5) less than the predetermined acceptable level.

72. The method of claim 71 wherein the measurements of step (6) are continuous.

73. The method of claim 72 wherein a potential difference equal to the threshold potential difference is measured in the sample of step (5) earlier than the preselected time of step (3), thereby indicating a level of bacterial contamination in the liquid sample of step (5) greater than the predetermined acceptable level.

74. The method of claim 71 wherein the liquid sample is selected from the group consisting of city water, river water, milk, suspensions of food solids, solutions of food solids, blood, urine, and industrial liquids.

75. The method of claims 71, 72 or 73 wherein the electron transporter is mixed with the liquid medium at a time no later than the time at which a change in potential would occur if the electron transporter had been mixed at the commencement of measurements.

76. The method of claims 71, 72 or 73 wherein the bacteria are aerobic.

77. The method of claims 71, 72 or 73 wherein the bacteria are optionally aerobic.

78. The method of claims 71, 72 or 73 wherein the bacteria are selected from the group consisting of *E. Coli, Staphylococcus aureus, Staphylococcus epidermidis*, and *Salmonella typhimurium*.

79. The method of claims 71, 72 or 73 wherein the metabolic route is the route by which alpha-ketonic acids are decarboxylated.

80. The method of claim 79 wherein the alpha-ketonic acid is pyruvic acid.

81. The method of claims 71, 72 or 73 wherein the electron transporter is a coenzyme.

82. The method of claim 81 wherein the coenzyme is selected from those coenzymes which are a known part of the metabolic route by which alpha-ketonic acids are decarboxylated.

83. The method of claim 82 wherein the alpha-ketonic acid is pyruvic acid.

84. The method of claim 83 wherein the coenzyme is selected from the group consisting of lipoic acid, NAD and FAD.

85. The method of claim 81 wherein the electron transporter is in the oxidized form.

86. The method of claims 71, 72 or 73 wherein the electron transporter is a cofactor.

87. The method of claims 71, 72 or 73 wherein the energy substrate is a constituent sugar.

88. The method of claim 87 wherein the sugar is glucose.

89. The method of claim 87 wherein the sugar is lactose.

90. The method of claims 71, 72 or 73 wherein the energy substrate is an adaptive sugar.

91. The method of claim 90 wherein the adaptive sugar is selected from the group consisting of xylose, maltose, galactose, and arabinose.

92. A composition for monitoring aerobic or anaerobic cells, cellular fractions or organites in a medium, said composition comprising:
(a) an energy substrate capable of promoting the growth of said cells, and
(b) lipoic acid as an electron transporter and oxidoreduction indicator, whereby cellular activity is determined by the proportion of the oxidized and reduced forms of the lipoic acid.

93. The composition of claim 92 wherein the composition has sufficient ionic conductivy to permit potentiometric measurements and a pH buffered about 7.0.

94. The composition of claim 92 wherein the energy substrate is a sugar.

95. The composition of claim 94 wherein the sugar is glucose.

96. The composition of claim 92 which is liquid.

97. The composition of claim 96 which is concentrated, thereby allowing for dilution for use.

* * * * *